United States Patent [19]
Pratt, Jr.

[11] 3,941,670
[45] Mar. 2, 1976

[54] METHOD OF ALTERING BIOLOGICAL AND CHEMICAL ACTIVITY OF MOLECULAR SPECIES

[75] Inventor: George W. Pratt, Jr., Wayland, Mass.

[73] Assignee: Massachusetts Institute of Technology, Cambridge, Mass.

[22] Filed: Nov. 12, 1970

[21] Appl. No.: 88,528

[52] U.S. Cl............ 204/158 R; 21/54 R; 21/102 R; 21/DIG. 2; 204/157.1 R; 204/159.11; 204/162 R; 204/DIG. 11; 426/237
[51] Int. Cl.$^2$..... A21D 6/00; A61L 1/00; B01J 1/10
[58] Field of Search.. 204/DIG. 11, 158 R, 157.1 R, 204/162 R, 159.11 T; 21/102 R, 54 R, DIG. 2; 99/107, 217, 218; 195/78, 79, 112; 426/234, 237

[56] References Cited
UNITED STATES PATENTS

| | | | |
|---|---|---|---|
| 3,233,964 | 2/1966 | Skoldberg | 21/61 |
| 3,600,291 | 8/1971 | Wiley | 204/162 |
| 3,702,973 | 11/1972 | Daugherty et al. | 204/176 |
| 3,719,454 | 3/1973 | Shang | 204/DIG. 11 |
| 3,817,703 | 6/1974 | Atwood | 21/102 R |

FOREIGN PATENTS OR APPLICATIONS 671,922   5/1952   United Kingdom..................... 21/54

OTHER PUBLICATIONS

McGuff et al., Medical & Biological Illustration, Vol. 16 (1966), pp. 191–194.
Elion, Laser Systems & Applications (1967), pp. 79–81.
Electronics, Vol. 34, Nov. 24, 1961, pp. 54–57.
Nature, No. 4965 (Dec. 16, 1964), p. 1295.

Primary Examiner—Howard S. Williams
Attorney, Agent, or Firm—Arthur A. Smith, Jr.; Robert Shaw; Martin M. Santa

[57] ABSTRACT

A method of altering (i.e., deactivating or activating) the biological activity of macromolecular species that employs laser beam radiation at a frequency that excites vibrational and rotational states of the irradiated species and at an intensity sufficient to activate the species (but below the denaturation level) or to a level such that the weak bonds—e.g., hydrogen bonds—that determine the spatial character, and hence the biological activity of macromolecules are irreversibly broken to such extent that the macromolecule loses its original form (the process of denaturation) and assumes an inactive (denatured) configuration. In the case of absorbing materials, pulses of energy from the beam, which are obtained by interrupting a c.w. beam, using a pulsed laser, or as a Q-switched configuration, are used. In a broad sense, the invention is primarily directed to the breakdown of large molecules either into varieties with different spatial characteristics or into smaller molecular units. This is effected by exposure to laser radiation which excites vibrational and rotational states of the irradiated species to such an extent that substantially irreversible chemical changes take place. These changes can in some instances occur in the species itself without the presence of any other reacting chemical agents. In other instances, the laser may effect a change by enhancing or retarding a chemical reaction among different species.

36 Claims, 17 Drawing Figures

W = 2S SIN θ

INVENTOR:
GEORGE W. PRATT, JR.

BY

ATTORNEY

INVENTOR:
GEORGE W. PRATT, JR.
BY
ATTORNEY

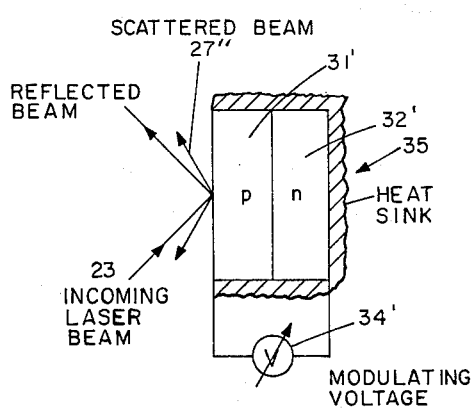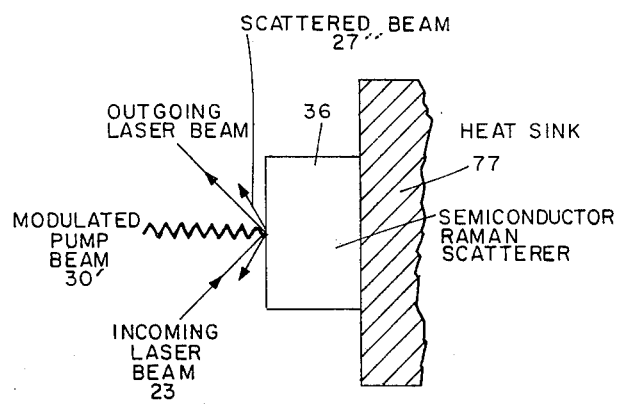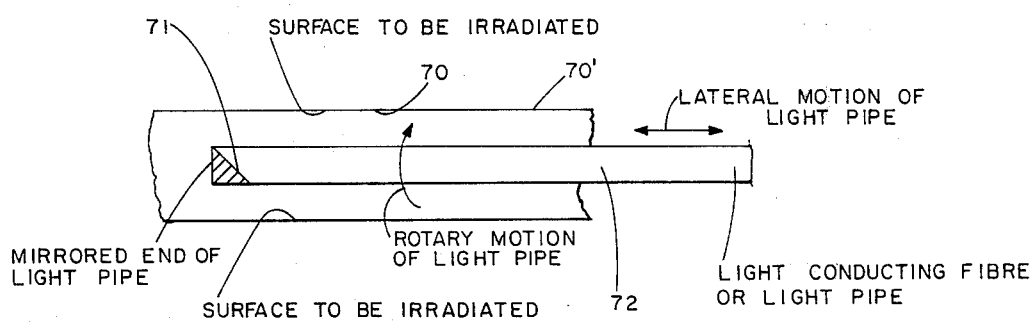

INVENTOR:
GEORGE W. PRATT, JR.
BY
ATTORNEY

METHOD OF ALTERING BIOLOGICAL AND CHEMICAL ACTIVITY OF MOLECULAR SPECIES

The present invention relates to methods of and means for altering the activity the macromolecular species by exposing said species to laser radiation in a particular frequency range to excite rotational and vibrational levels in the species at a particular intensity level and for a sufficient period of time to produce either reversible or irreversible changes therein; these changes can in some instances occur in the species itself without the presence of any other chemical agent as, for example, in the process of inactivation, or in other cases the radiation may enhance or retard a chemical reaction by activating one or more participants.

It has been known that electromagnetic radiation can alter the chemical and/or biological properties of many substances. Thus, for example, sterilization by gamma rays, $\beta$-rays, x-rays and ultra violet light have been extensively investigated. The discovery underlying the present invention is that infrared radiation in a relatively narrow band of frequencies (e.g., 3 to 30 microns) introduced into the vibrational and/or rotational states of certain complex organic molecules has an unusually large influence upon the irradiated molecules. The process hereinafter described employs high energy infrared laser radiation sources which, by way of illustration, can be a $CO_2$ laser which can produce c.w. radiation levels in the kilowatt range and pulses in the megawatt power range. Furthermore, it is now possible to tune the frequency of high power infrared lasers over a considerable range (5 microns to 20 microns). These high powers over a range of frequencies allow the efficient transfer of large amounts of energy into macromolecular organic systems. It has been found for present purposes that this energy transfer can be due to absorption of the laser radiation into electronic levels of the molecules, but, also, and more importantly, into the excitation of vibrational and rotational levels. Furthermore, the high power densitites available allow the absorption of significant amounts of power.

The Raman spectra of many amino acids, nucleic acids, and biopolymers that are the molecular structures of greatest interest herein, have vibrational and rotational absorptions in a range from 350 $cm^{-1}$ to 3,500 $cm^{-1}$, more or less. There is a non-linear coupling of a vibrating molecular bond to an electromagnetic ambient field of appropriate frequency. In order that the field induce amplitudes of vibration or rotation so large that molecular bonds will be either reversibly or irreversibly broken, an intense radiation source is necessary and preferably one that can be tuned to obtain any resonant enhancement possible. Lasers operating in the above frequency range, e.g., $CO_2$ lasers which operate at 10.6 microns and CO lasers which operate in a range from 5.2 to 6 microns, are ideal radiation sources. Not only are they capable of delivering enormous pulse powers, e.g., in the megawatt range, and very large c.w. powers, e.g., in the kilowatt range, but they can also be tuned, for example, using frequency doubling techniques and spin-flip Raman scattering.

Tunable Raman scattering may be accomplished in at least two ways. First, it is possible to tune continuous stimulated spin-flip Raman scattering, e.g., in Insb as reported by Mooradian et al. (Appl. Phys. Lett, 1970). Secondly, it is possible to vary the elastic constants of the Raman scatterer by altering its carrier concentration which in turn alters the elastic constants of the scatterer and hence its vibrational frequencies, as hereinafter discussed.

It should be further noted that the biological activity of many macromolecular species or biopolymers depends upon rather weak bonds as discussed in Chapter IV of J. D. Watson's book "Molecular Biology of the Gene." These bonds can be effectively broken by exposure of the macromolecule to laser radiation either by direct absorption of the energy or indirectly. The indirect process starts with the absorption of electromagnetic radiation by vibrational and/or rotational modes involving covalently bound atoms. For example the skeletal frequencies lying in the 800 to 1,150 $cm^{-1}$ range for Ribonuclease or the "breathing" mode of the monosubstituted phenyl ring at 1,006 $cm^{-1}$ in phenyl alanine would be strongly excited by a $CO_2$ laser operating at 10.6 or 9.6 microns. Large amplitude oscillations of this type can lead to the destruction of weaker bonds and cause the molecule to lose its original form, i.e., become denatured or deactivated by assuming an inactive configuration. This is to be contrasted with burning wherein the process of combustion occurs.

The invention disclosed herein is described in greatest detail in connection with sterilization whereby macromolecular configurations are deactivated by laser radiation. It is to be noted, however, that some aspects of the present teaching make it useful in connection with processes wherein such macromolecules are activated. The sterilization process has been found to be particularly useful in connection with the deactivation of dry Bacillus subtilis spores. In tests conducted in connection with the present invention, a spore sample of approximately $10^7$ spores distributed over 3 $cm^2$ on acetate paper was exposed to an unfocused $CO_2$ laser beam of 23 watts power for 1/10 of a second. All the spores struck by the beam were rendered completely inactive. That is to be compared with required exposure times 600 to 10,000 times longer in steam at 170° C to obtain the same effect. In similar tests, exposure of a paper substrate to the same laser beam for 1/25 of a second did not burn or otherwise substantially damage the paper.

Infra red radiation is almost totally reflected from metallic surfaces. Consequently, a metallic or other highly reflecting object can be exposed to an intense laser beam for prolonged periods of time, seconds or hundreds of seconds depending on the laser power, without the transfer of damaging amounts of energy to the reflecting material. Electromagnetic waves incident upon a metallic surface combine with reflected waves to produce a vanishing tangential electric field for an ideal metal. For normal incidence the tangential component of the electric field reaches a maximum at odd multiples of $\lambda/4$, where $\lambda$ is the wavelength of the radiation. For a $CO_2$ laser $\lambda = 10.6$ microns. Consequently, macromolecular species of size considerable less than $\lambda/4$ in extent from the metal surface would lie on a space of low electric field and would be unable effectively to couple to and absorb energy from the laser beam. Consequently, oblique incidence of the laser beam to the metal surface is used. It can be shown that the electromagnetic field is then described as a combination of a standing and travelling wave. Wherever the tangential component of the E field vanishes, the normal component reaches a maximum, and, when the normal component vanishes, the tangential component is a maximum.

Infrared laser radiation incident obliquely on a metallic or other highly reflecting surface provides an excellent means for rendering that surface sterile, which is useful in sterilizing surgical instruments, metallic vessels and tanks, metallic pipes, needles, etc. This radiation process is accomplished by sweeping the beam over the surface of these objects by moving the laser, using moving mirrors, or moving the object itself or any combination of these means, as later discussed. A further important use for the present teaching is the sterilization of highly reflective packaging material such as aluminum foil. The foil is passed under the beam in such a way that the entire area required to be sterile is exposed to the beam. In order that the laser beam intercept as large an area as practical for a given position of the surface and laser, the laser beam can be reflected obliquely back and forth between the foil surface and a reflecting surface as hereinafter discussed.

Accordingly, a principal object or the present invention is to provide a new and useful method of sterlization, one which employs laser radiation of particular frequencies, intensities, and time durations.

The energy required to deactivate surface contaminants is small compared to that required to significantly damage an absorbing material. Therefore, the invention can be used to sterilize plastics, cloth, glass, as well as foodstuffs that are subject to spoilage or other deterioration due to surface contamination. A particularly useful technique when dealing with such absorbing material is the use of high energy, short time duration laser pulses achieved by operation of the laser in a pulsed or Q-switched configuration. Still another object of the invention, therefore, is to provide laser apparatus adapted to irradiate macromolecular species disposed on surfaces of materials which are attacked by the laser radiation, but to maintain the level of intensity or time of exposure, or a combination thereof below magnitudes sufficient to cause undesirable damage to the absorbing surface.

A further object is to provide laser apparatus adapted to irradiate macromolecular species and in particular those responsible for infection such as viruses, bacteria, and the like, as well as bacteria and enzymes which may be disposed on reflecting or absorbing surfaces, in partially transparent liquids or in gases; this aspect of the invention has particular application in medical situations in operating rooms and the like wherein a sterile atmosphere is highly desirable such as burn recovery and certain types of surgical procedures, in the process of pasteurization, and for the purpose of controlling a process such as fermentation.

A still further object is to provide laser apparatus adapted to sterilize flesh laid bare in a medical procedure where surface contamination of the bare tissue is to be prevented; in this instance the laser is pulsed so that only a monomolecular layer of tissue and the contaminants thereon are biologically deactivated.

The foregoing objects may be classified loosely as being directed to a method of activating (i.e., changing the level of activity thereof) or deactivating (i.e., inactivating) biological type macromolecules. The invention has use, however, in connection with other molecular species as well. Thus, by way of illustration, it can be used to perform catalytic action in an oil cracking operation wherein complex molecules are broken down into less complex molecules. Broadly, therefore, the objects of the invention are to teach a method of irradiation of a macromolecular or complex molecule species wherein laser radiation is introduced into the vibrational and/or rotational states of the species thereby to affect the activity of the irradiated molecules.

Yet another aspect of the invention is that of activating molecules to change, for example, the rates at which spores, viruses and the like multiply or to change the rate at which less complex molecules enter into chemical reactions; this is accomplished, again, by introducing laser radiation at a frequency which excites the vibrational and rotational states of the irradiated species, but in this instance the intensity of such radiation is kept below a level which would deactivate spores, viruses and living molecules and below a level which would change the form of the less complex molecules.

Since, as above mentioned, particular frequencies of laser radiation or a particular band of frequencies may best serve the purposes herein discussed, it is necessary to provide such frequencies or sweep the band of frequencies to function as intended. A still further object is, therefore, the provide in laser apparatus, means for choosing a particular frequency output and for shifting or sweeping that output as well as to provide means for detecting the effect of such radiation as a function of frequency, intensity, etc.

These and still further objects will be evident upon reference to the descriptive portion of the specification hereinafter and are particularly delineated in the appended claims.

By way of summary, the objects are embraced by a process for altering (i.e., deactivating and activating) the biological activity of macromolecular species (e.g., living cells, enzymes, spores, viruses, bacteria and other cells and combinations of cells) and the chemical activity of further molecular species (e.g., high molecular weight hydrocarbons), the process, in the latter case, acting, in effect, like a catalyst. The species are subjected to laser radiation at a frequency that excites the vibrational and rotational states thereof; for example, in a case of spores, etc. a frequency of interest is the 10.6 micron output of the $CO_2$ laser. The intensity of radiation is maintained at the level high enough to effect such altering, but the level of such intensity and the time of exposure are kept to less than some combination which would affect adversely the material upon which the species rest or at an appropriate level to provide desired catalytic action. The intensity level and time duration aspect is of consequence in pasteurization or sterilization uses of the process wherein the species is located on plastic, paper and the like which are destructible by laser frequencies and intensities of the range most useful in the sterilization or pasteurization process herein described; or when the species is in a fluid containing one or more constituents which are destructible by laser frequencies and intensities of the range most useful in the sterilization or pasteurization process herein described.

The invention is described hereinafter upon reference to the accompanying drawings in which:

FIG. 1 is a diagrammatic representation of an embodiment of the present invention and shows, schematically, a laser apparatus adapted to irradiate a target with Q-switched radiation which may be passed into a frequency selecting or tuning device whose output is directed onto the target;

FIG. 2 shows, diagrammatically, an arrangement whereby the characteristically small laser beam, which may arise from the laser of FIG. 1, is reflected between the surfaces of reflecting plates or other media so as to fill the entire volume between the plates defined by the cross-hatched area in the x-y plane and of thickness $t$ in the z direction, $t$ being the thickness in the z direction of the incoming laser beam, whose width in the x-y plane is W as shown;

FIG. 9b is a modification of the apparatus of FIG. 9a;

FIG. 12 shows, schematically, apparatus used to frequency shift and frequency modulate an incoming laser beam by varying the elastic constants of a semiconductor forming part of a diode whose bias is supplied by a modulated voltage source, the modulated signal appearing in the scattered beam;

Figure 15:
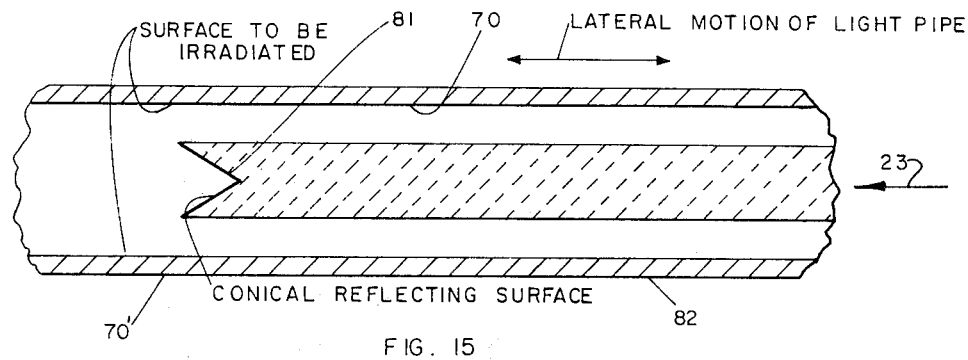
Figure 16:
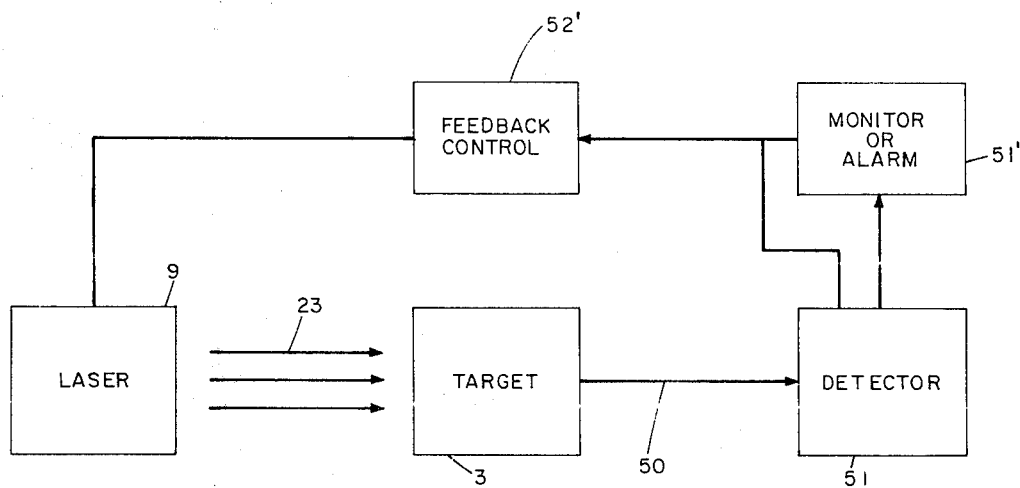

FIG. 13 shows, schematically, apparatus used to frequency shift and frequency modulate an incoming laser beam by varying the elastic constants of a semiconductor wherein the incident beam is directed to an area also illuminated by an amplitude modulated pump beam which alters the electron-hole concentrations in the region where it is absorbed, the amplitude modulated pump signal being converted into a frequency modulated scattered laser beam;

FIG. 14 is a diagrammatic representation of a light conducting fibre or pipe used to convey sterilizing radiation to the interior walls of a tubular surface, the entire wall area being swept by the light beam by rotating the light pipe whose end is mirrored at an angle so as to divert the reflected light to the walls, the light pipe being allowed to move in a lateral fashion into and out of the tubular cavity;

FIG. 15 is a diagrammatic representation, partially cutaway, similar to the representation in FIG. 14 except that the light beam is reflected by a conical surface; and FIG. 16 shows in block diagram form, an arrangement whereby laser radiation directed upon a target area is reflected, transmitted or scattered and detected, and the detected radiation functions as an output or as a control signal.

Figure 1:
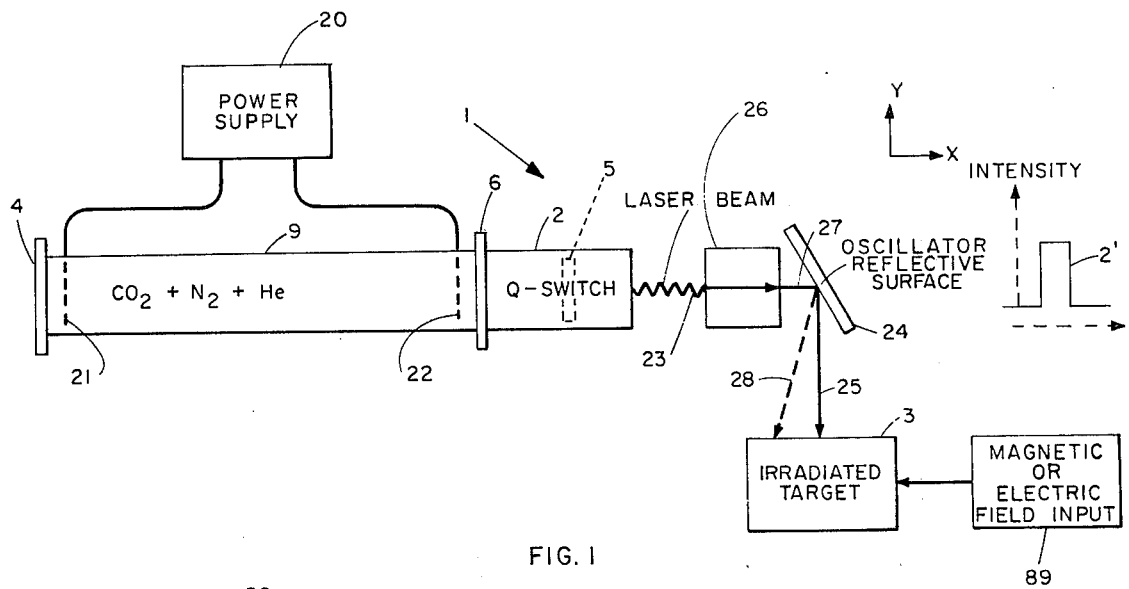
Figure 6:
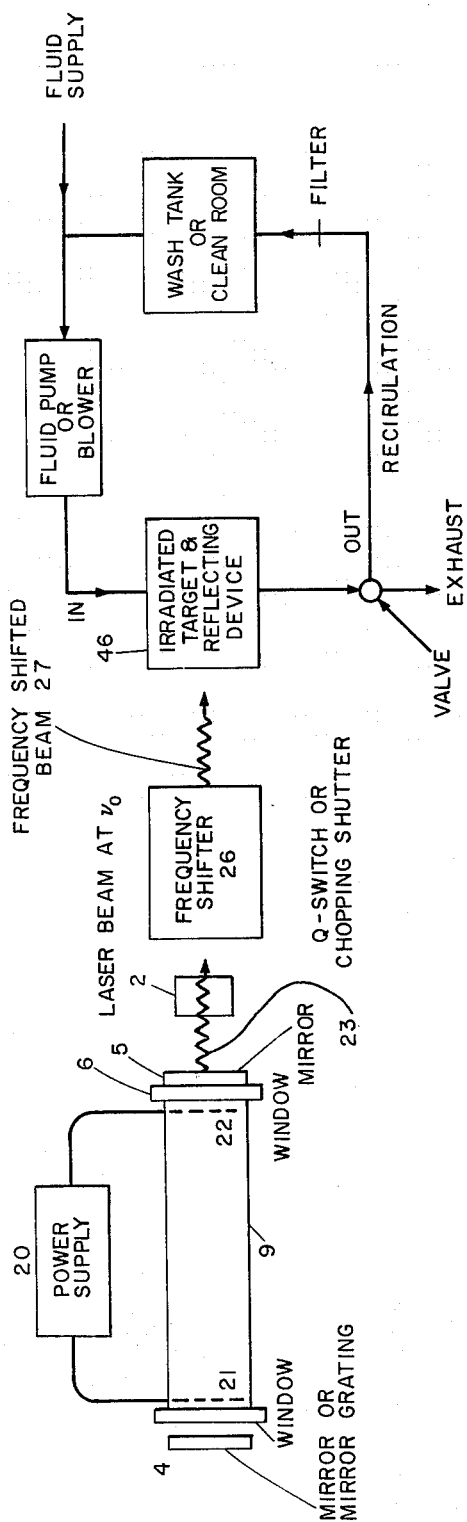
FIG. 6 is an embodiment similar to FIG. 1 in which the beam may or may not be Q-switched or pulsed and the particular frequency may be selected by using the left-hand mirror or mirror-grating combination and/or frequency shifts might be produced by a Raman scattering cell to provide the beam which finally impinges upon a target.
Figure 11:
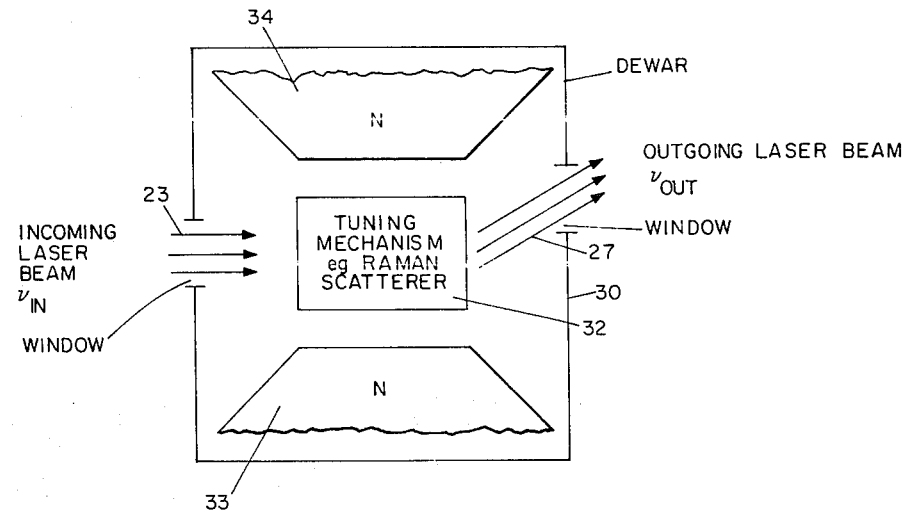
FIG. 11 shows, schematically, an arrangement for altering the frequency of a laser beam to select a particular frequency using a Raman scattering cell, the Raman scattering being tuned by using a magnetic field to alter spin flip Raman scattering frequencies or by varying the elastic constants of the scatterer.

Turning now to FIG. 1, apparatus is shown generally at 1 for altering (deactivating or activating) the biological and/or chemical activity of macromolecular species which may be located in the block labeled 3 and described as an irradiated target. Such altering, as discussed above, is effected by irradiating the macromolecular species by directing thereupon radiation from a $CO_2$ laser 9 (that contains $CO_2$ as well as $N_2$ and He gases) which produces, by the process of stimulated emission, radiation primarily at 960.99 $cm^{-1}$ and 1063.77 $cm^{-1}$. The laser 9 may be Q-switched as shown at 2 to provide short, intense bursts of radiation. The emitted radiation numbered 23 may further be frequency shifted, modulated, or tuned by a device 26. The radiation is directed upon the target 3 by a mirror arrangement 24 which may be capable of oscillatory motion for the purpose of sweeping the beam over the target. Work done to date has been primarily with dry Bacillus subtilus spores, as later discussed herein, which are made up at least in part of macromolecular species or biopolymers which control the biological activity of said spores. The deactivation of said spores is an important aspect of the present invention. Radiation from the laser 9 excites vibrational and rotational states of the irradiated spores located at the target 3, the large amplitudes of induced oscillation in the spores being sufficient to disrupt these macromolecules to the extent that they are no longer biologically active. This disruption and disorientation is physical or mechanical and is not of the nature of the chemical reaction that obtains in a burning process. Said another way, the spores are inactivated but not necessarily (or desirably) burned. This inactivation can be effected by correlating the time of exposure and beam intensity, by the use, for example, of a shutter or a chopper to pass and not pass the beam, or by the use of the Q-switch 2 which produces a very high intensity, but very short pulse 2'. The Q-switch embodies a rotatable mirror 5 forming a cavity which emits radiation at one angular position only thereof and is capable of quite large intensity build-up between pulses. The frequency shifter, selector, or modulator at 26 is used to pick out radiation whose frequency is particularly adapted to inactivate or activate the target. The optical cavity in the embodiment of FIG. 1 is between the mirror 5 and a mirror 4. The mirror 4 can be a grating which can also be used as a frequency selector by varying the angle at which radiation strikes the grating.

The optical cavity defined by the mirror or mirror-grating 4 and the mirror 5 which, as mentioned, may include a Q-switch, contains a gaseous medium adapted to receive energy from electrodes 21 and 22 energized by a d-c power supply 20 to produce, in the enclosed space within the gaseous laser medium between the mirror or mirror-grating combination 4 and a window 6, an inverted population of energy states so that electromagnetic radiation therein is amplified by the process of stimulated emission. The reflecting surface 5 is partially transparent to allow the laser beam 23 to emit from the optical cavity. The beam 23 in FIG. 1 and in FIG. 6 is shown entering a frequency shifting device 26 which may be used to select a frequency particularly adapted to be effective upon the target to-be-irradiated, although frequency shifting is not always necessary. The frequency shifted beam labeled 27 in FIG. 1, is shown reflected by the oscillatory reflective surface 24 to cover a portion of the target between the position shown at 25 and 28, respectively, thereby to spread over a larger area the characteristically small laser beam. This oscillation is shown to be in the x-y plane but it can go into the y-z plane, as well. The target may be moved, as well, to effect a greater coverage by the laser beam. The laser 1, as mentioned, lases at 10.6 microns, primarily. However, other frequencies may be selected by use of a grating-mirror combination 4 in which the angle of the grating is varied to provide effective optical feedback to the cavity at frequencies which vary with the position of the grating. Further control of the frequency may be achieved by the frequency shifting, or modulating, or tuning device 26 which may be one of several mechanisms. One such means for shifting the frequency is to employ at 26 spin flip Raman scattering of the entering laser beam 23, as shown in FIG. 11, by an InSb crystal 32 suitably cooled by liquid nitrogen and placed in a variable magnetic field (represented by pole pieces 33 and 34) whose strength determines (the order of 10,000 gauss), at least in part, the frequency of the Raman scattered beam. (The Raman scatterer 32 can also be a ferroelectric such as $BatiO_3$, $LiNbO_3$, and the elements 33 and 34 can be plates electrically charged to provide a field the order of kilovolts/cm.) Another means of shifting the frequency is to use Raman scattering wherein the elastic constants of the Raman scatterer are changed or modulated as shown in FIGS. 12 and 13. In FIG. 12 the elastic constants of the p-side of a diode 35 are varied by varying the voltage output of a potential source 34' applied between the p-side numbered 31' and the n-side numbered 32'. The scattered beam labeled 27'' is frequency modulated as a consequence of modulating the elastic constants of the crystal 35. The device can be arranged so that the beam 23 strikes the n-side 32' instead of the p-side 31'. In FIG. 13, the elastic constants of a semiconductor scatterer 36 are varied by subjecting the scatterer 36 to a modulated pump beam 30' which alters the number of electrons and holes in the scatterer 36 which is temperature controlled by a heat sink 77. The pump beam 30' is arranged to strike the scatterer at the same spot struck by the incident beam 23. The variation of elastic constants with carrier concentration is detailed in a work of R. W. Keyes, I.B.M. Journal 5, 266 (1961). By the foregoing methods the frequency of the beam can be swept so as to in react effectively with the vibrational and/or rotational levels of the target materials. The frequency modulation methods discussed above are also useful in the transmission of information in communications.

Figure 2:
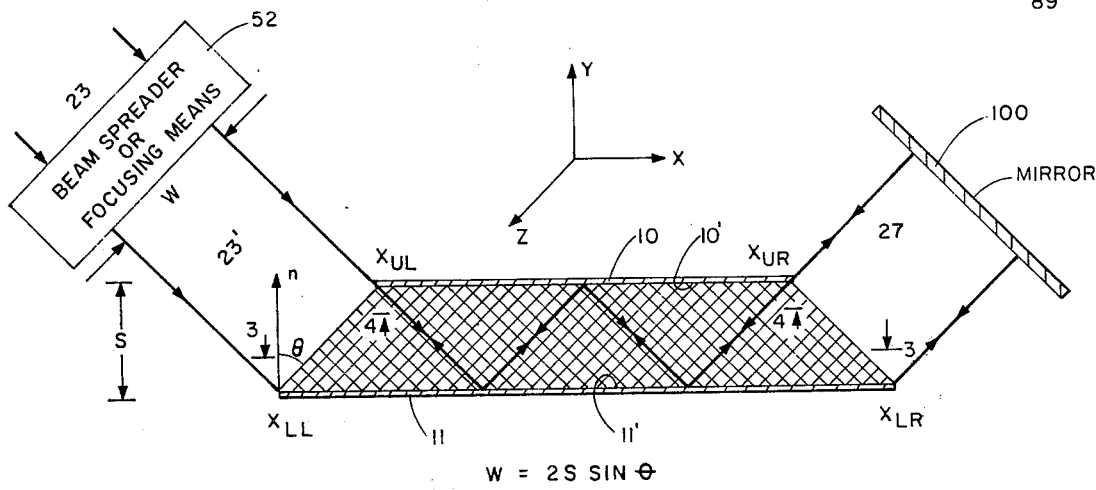
Figure 3:
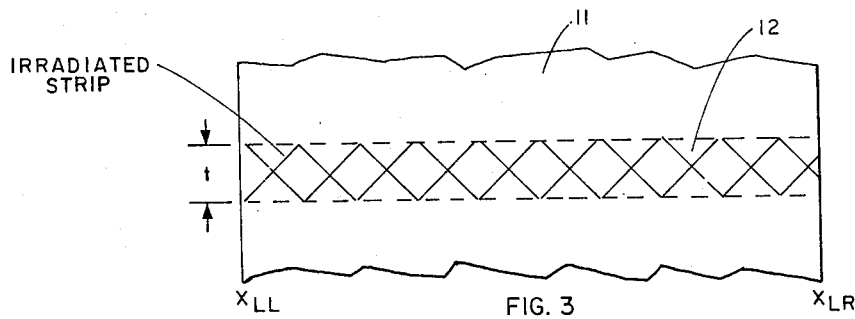
FIG. 3 is a view taken upon the line 3—3 in FIG. 2 looking in the direction of the arrows.
Figure 4:
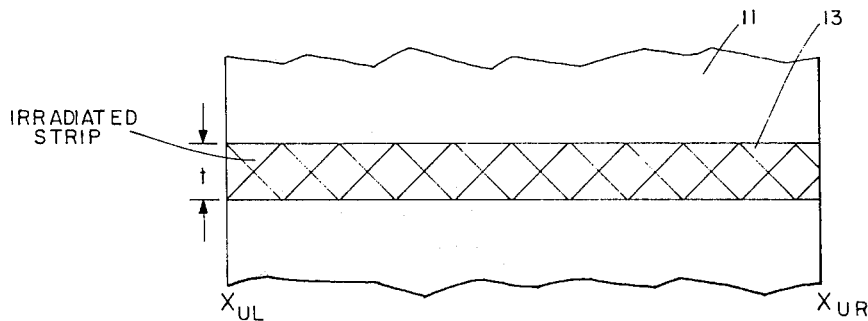
FIG. 4 is a view taken upon the line 4—4 in FIG. 2 looking in the direction of the arrows.
Figure 5:
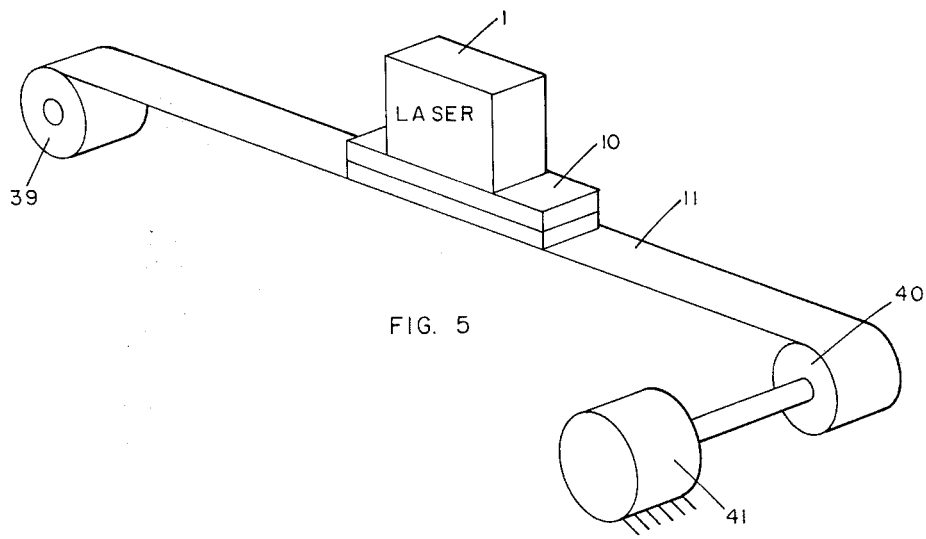
FIG. 5 shows, schematically, an arrangement for effecting longitudinal movement of the target material of FIG. 1 which appears as a strip, foil, or ribbon in FIG. 5, transverse motion between the beam and strip material being accomplished, for example, by a pivoting mirror scheme as indicated in FIG. 1.

In FIG. 2 the laser radiation 23 is shown entering a beam expander or focussing means 52 the output beam 23' from which is directed upon the reflecting surface 11' of a moving sheet or metal strip 11 in order to sterilize that reflecting surface. (The sheet 11 can contain a thin liquid film upon the surface 11', as later mentioned, to provide exposure of the film and any macromolecules carried therein to selective radiation frequencies thereby to affect the carried molecules.) The radiation in the illustrative example has cross dimensions W and is directed at an angle $\theta$ to the normal $n$ to the planar surface of the strip 11. A sheet 10 having lower surface 10' is shown disposed in a closely-spaced plane parallel to the plane of the surface 11'. The beam is directed at the surface 11' at an angle $\theta$ no greater than $\sin^{-1} W/2S$, where S is the distance between the upper surface of 11' of the strip 11 and the lower surface 10' of the sheet 10. In actual apparatus, the reflecting strip or ribbon 11 may be moving sheet of aluminum foil or other material which it is desired to sterilize on the upper surface thereof as the foil moves from a roll 39 to a roll 40, as shown in FIG. 5, the roll 40 being driven by an electric drive designated 41. The laser beam is shown reflecting back into the space between the upper surface 10' and the lower surface 11' by a mirror 100; the reflected beam can be caused to pass back across the surfaces to irradiate other strips similar to the strips designated 12 and 13 in FIGS. 3 and 4. In FIG. 2 the ribbon 11 moves longitudinally (i.e. the z direction) into or out of the paper and the beam is reflected to move transversely (i.e., the x direction) of the moving sheet 11.

Figure 7:
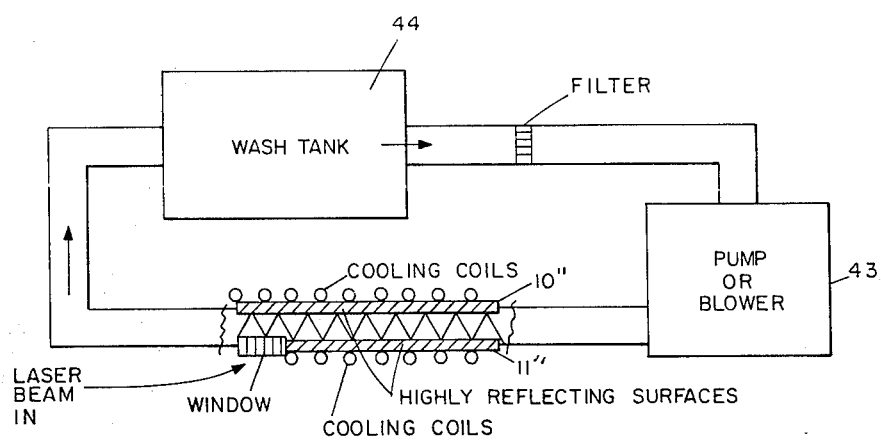
FIG. 7 is a diagrammatic representation of apparatus wherein a liquid is used to wash an object and the liquid which is partially transparent to the beam is thereafter sterilized by a laser beam, the representation being intended to illustrate, as well, apparatus adapted to pass air or some other gas past the laser beam.
Figure 8:
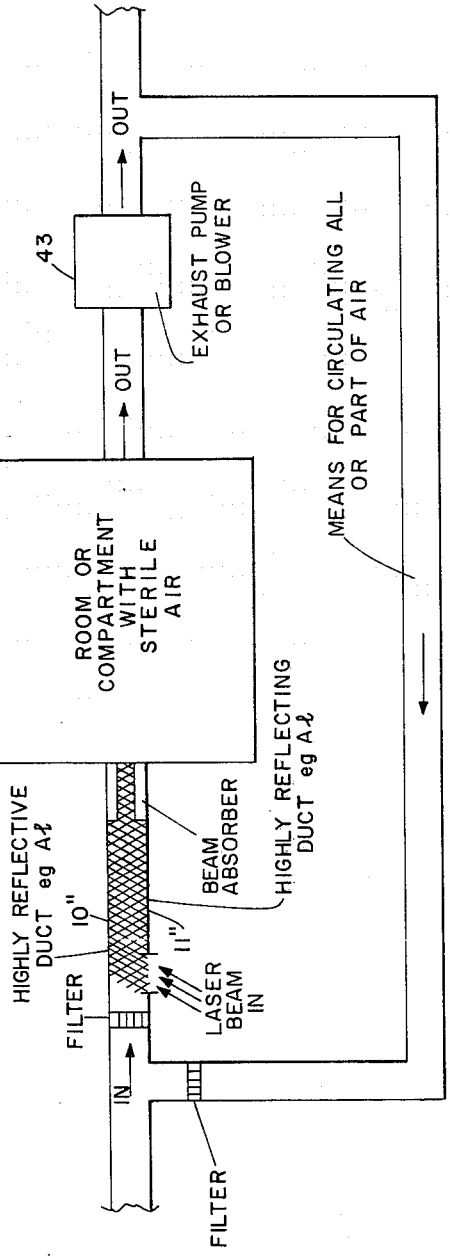
FIG. 8 is a further diagrammatic representation of apparatus wherein the air entering a room is sterilized by passing through a duct filled with radiation.

Of course, neither the upper nor the lower surface need move and the gap therebetween can contain a gas, such as air, or a liquid which can be sterilized as it passes between the reflective surfaces; and the arrangement shown diagrammatically in FIGS. 7 and 8 can be used. In these figures a pump 43 moves a fluid, gas or partially absorbant liquid, into the region between the reflecting surfaces of an upper plate 10'' and a lower plate 11''. The fluid can be a liquid used in connection with a washing operation in a wash tank 44 in FIG. 7; or the element 43 can be a blower and the fluid can be a gas recirculated from an operating room 45 in a hospital for sterilization by the laser beam of the room air, as shown in FIG. 8. The sterilization of the air or other fluid as it passes between the plates 10'' and 11'' is accomplished because of the rapid biological inactivation possible using laser beams of appropriate frequencies, as discovered by the present inventor and as discussed herein. The process is particularly useful in sterilizing air because spores and the like carried by air are physically separated from one another and the inactivation thereof can be effected in milliseconds or less; however, spores and the like located on material surfaces have some thickness and the outer layers tend to absorb the laser radiation and to protect the lower layers; also, spores and the like in water or some other solutions are somewhat protected by solution absorption of the radiant energy. Thus, higher beam intensities may be necessary adequately to expose multi-layer spores, or selective frequencies may be needed to inactivate spores in solution. The process is also useful in controlling the activity of enzymes in a process such as fermentation.

In the apparatus of FIG. 6, much of the apparatus shown is duplicative of FIG. 1 or other figures and to that extent the same number designations are applied;

other elements are merely named since, again, they are discussed elsewhere herein. The illustrative example shown does disclose, schematically, a more complete apparatus than in some of the other figures and does differ somewhat in other particulars. For example, a mirror 5' is shown at the right side of the optical cavity for use in instances in which the Q-switch 2 is replaced by a chopper or other device.

As discussed elsewhere herein, irradiation of a metal or other reflecting surface has the definite advantage of the reinforced electric field effect of the laser radiation near the surface. Also, a metal surface can be irradiated for a substantial time period to insure complete inactivation of the spores and the like in those instances in which there is some substantial thickness of the material to be inactivated. However, the principal value of the present discovery is the capability of the appropriate-frequency radiation of relatively modest intensity to inactivate or denature in a very, very short time period. This makes possible the sterilization of air and some other fluids, (e.g. Nujol, carbon disulphide ($CS_2$) and benzene ($C_6H_6$)) but it makes possible, as well, the sterilization of plastics and other substances that cannot be sterilized of such things as B. subtilus short of destruction of the substance, as by burning, since prior art practice requires exposure of the B. subtilus to 170° C temperature of the order of three hours. Thus, the present discovery allows faster sterilization, but it permits, as well, sterilization that was not heretofore possible (for example, paper is not suitable for heating in an autoclave under steam, however, sterilization of a paper surface is possible here). One more point is of interest. Mention has been made that the deactivation or denaturing process does not, or at least need not, involve burning or combustion of the spores, viruses, bacteria or cells denatured. For that reason, the deactivation time is quite short, and the amount of energy absorbed in the deactivation process is quite small. The inventor has found that life, even in the hard-to-deactivate spores and the like, can be terminated relatively easily by attacking the organism at its weakness.

In the foregoing discussion, the combination of exposure time and beam intensity is emphasized, and one way of controlling the magnitude of both is mentioned in connection with Q-switching. It should be evident from the discussion also that the laser beam can be c.w. and that the exposure time of macromolecules on the surface 11' in FIGS. 2–5 will be a function of the moving velocity of the strip 11; and, similarly, the exposure time of macromolecules in the embodiments of FIGS. 7 and 8 will depend upon the velocity of movement of the fluid between the plates 10" and 11". And in either situation the exposure time, of course, can be increased by reflecting the beam back and forth to create a plurality of strips 12, for example. Also, the intensity can be varied by a beam expander or focusing means 52 which can act upon the incoming beam 23 and provide the input beam 23' to the surface 11'. Tests have shown that even thin paper or cellulose samples such as thin filter material can be exposed to radiation of the order of 23 watts/cm² for 1/25 second without destroying the filter, and in tests conducted dry B. subtilus spores were inactivated as above discussed. The exposure time that a material will withstand depends, of course, on the mass of the material undergoing radiation as well as the material itself. Certainly, cellulose filters represent a class of easily damaged materials. The effect of the input radiation upon the backing material or the fluid within which the species is carried or the exposed species itself is determined also by the frequency of the input radiation, and recent developments have made very precise (the order of one hundred cycles or less) frequency control. Also, there is selective enhancement by non-linear coupling of a vibrating molecule of the species to the electromagnetic field of the input radiation as mentioned elsewhere herein.

Figure 10:
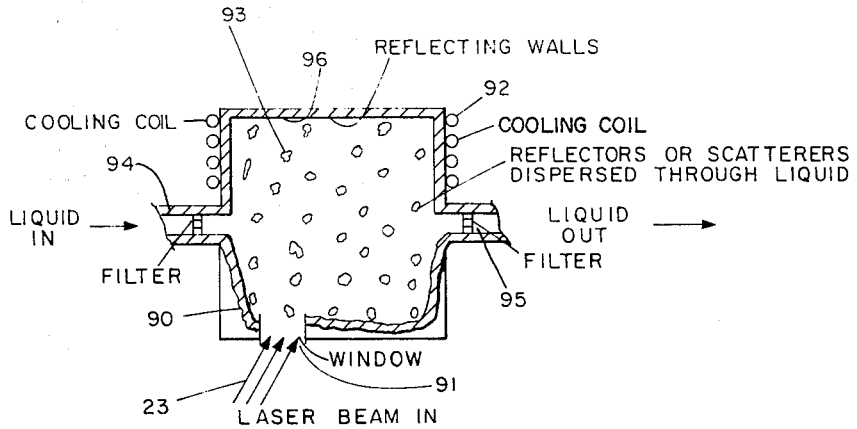
FIG. 10 shows an arrangement for scattering an incoming laser beam throughout a reflection cell (partially cutaway) by using reflecting bodies within the liquid in the cell, which are contained therein by the filters at the input and output ports of the cell.

The apparatus of FIG. 10 can be used in a system similar to that shown in FIG. 7 to replace the reflecting plates 10" and 11". In FIG. 10 the laser beam 23 is introduced to a cell or housing 90 through a window 91, as before, to pass into and through the liquid contained in said housing and be reflected by reflective walls 96. The radiation within the cell 90 is also scattered by reflectors 93 which are suspended in the liquid and kept in the cell by a pair of filters 94 and 95. In this way, the whole of the liquid within the cell volume receives the full intensity of the laser beam. A cooling coil 92 serves to remove laser introduced heat energy from the liquid. The embodiment of FIG. 10 is of particular use in a pasteurization process as, for example, in the production of alcoholic beverages. Again, the laser can be a $CO_2$ laser adapted to radiate principally at 10.6 and 9.6 microns; or a CO laser adapted to radiate at many frequencies between 5 and 6.2 microns; or a YAG: $Nd^{+3}$ solidstate laser adapted to radiate at about 1 micron. Also, the output radiation frequency from the particular laser used can be modulated and filtered to produce substantially one determined frequency and the amplitude can also be controlled, thereby selectively to affect particular macromolecular species (of many disposed within the liquid in the cell 90) while having a lesser effect on others; in addition, frequencies can be found to which the liquid is transparent. Furthermore, a detector as discussed in connection with FIG. 16 can be used to measure or determine the effect of the radiation on said particular species. Some aspects of the invention discussed in this paragraph have applicability in connection with the other embodiments discussed elsewhere herein.

Figure 9A:
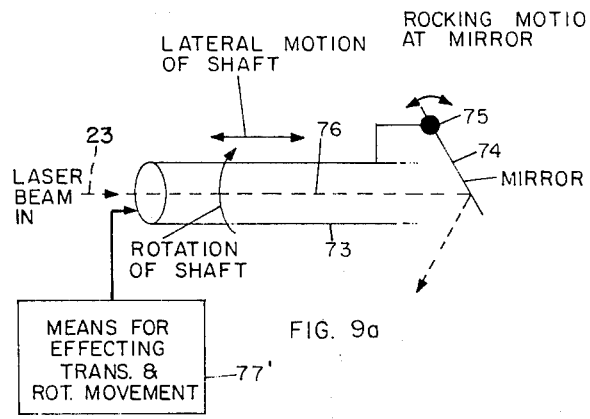
FIG. 9a is a diagrammatic representation of apparatus used to disperse and spread the beam over the walls of a surface which surrounds the device shown and said device may be moved into and out of a volume surrounded by the walls to-be-sterilized.
Figure 9B:
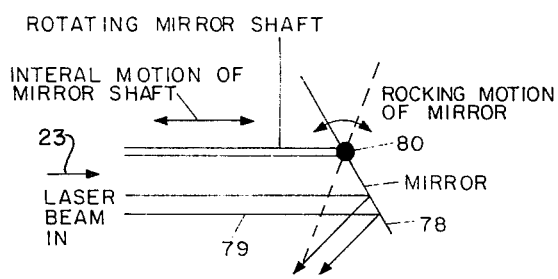

The discussion in this paragraph relates to apparatus adapted to irradiate the inner surface of a cavity (large or small) which may be a cylinder, container, vessel or even a region within the human body, the purpose of such irradiation being, broadly, to affect biological activity in the region of such irradiation. One such apparatus is shown in FIG. 9a, wherein the laser radiation 23 is shown directed into a light pipe 73 to be reflected by a mirror 74 pivotally attached at 75 to the light pipe. As is indicated in the figure, the light pipe 73 can be moved laterally along its axis 76 or rotationally about its axis. Means for effecting lateral and rotational movement of the pipe 73 is shown in block diagram form at 77'. In FIG. 9b, a mirror 78 is shown pivotally attached at 80 to a hollow shaft 79 adapted to vibrate to the left and right in FIG. 9b and to rotate. The light pipe can be the light conducting fibre shown at 72 in FIG. 14 and having a mirrored end surface 71 inclined to the fibre axis to reflect incoming light to the interior surface 70 of a cylinder 70'. Again, the pipe is capable of axial and/or rotational movement. A similar light pipe or fibre is shown at 82 in FIG. 15. The light pipe or fibre 82 has an inwardly axially oriented conical reflecting surface 81 at its terminating end adapted to spread the incoming beam 23 to the inner surface of the cylinder 70', as before.

The deactivation process discussed in greatest detail herein is concerned with very large molecules such as the double helix type discussed in the Watson reference, spores, etc. Such macromolecules contain hydrogen bonds which are the bonds generally disrupted by the input radiation (but are not necessarily the bonds which couple to the input radiations); this hydrogen bond is a dipole and is one which couples quite readily with radiation of appropriate frequency. The deactivating process is one wherein a relatively small amount of laser irradiation acts to disrupt the bond and the actual deactivation is effected then by the normal thermal type agitation which is always present in these species but which is, normally, not of destructive proportions. Said another way, the laser radiation acts to disrupt the binding forces of the molecules and allows the molecules to be torn asunder by the other forces which act within these complex molecules. Thus, a relatively small packet of laser radiation can perform the deactivation function. This is to be contrasted with burning wherein energy is introduced primarily to the electronic levels of the molecules and in which the resulting action is chemical, requiring the presence of other chemicals.

Another aspect of the invention is that of activating molecules to change, for example, the rates at which spores, viruses and the like multiply or to change the rate at which enzymes and less complex molecules enter into chemical reactions. This is accomplished, again, by introducing laser radiation at a frequency which excites the vibrational and rotational states of the irradiated species, but in this instance the intensity of such radiation is kept below a level which would change the form of the molecules. The activating process may be likened to that of a catalyst in chemical processes whereby a chemical reaction can be made to occur with greater facility. By way of further illustration, the activating process is useful in the petroleum cracking industry wherein complex molecules are broken down into less complex molecular structures.

The thermal agitation before discussed can be replaced by other forces such as high magnetic background fields (i.e., 12,000 gauss and up) and high field gradients (the order of 1,300 kilogauss per centimeter) to provide a dividing or other force; and such field can be a high electric background field as well. Both fields are represented by the block shown at 89 in FIG. 1. Or the species acted upon can be subjected to a high stress in the form of a pressure or shock wave to provide and enhance the dividing force. Such shock wave can be produced by wellknown mechanical means. Also, the laser beam itself can create pressure or shock waves in gaseous, liquid and solid media. Such shock waves can best be provided by Q-switching or pulsing the laser to provide very short exposure of the gas, liquid or solid to very high intensity laser radiation. In this way, the laser provides the irradiating means as well as the shock generating or creating means. The medium can be in a substantial volume, as the fluids shown in FIGS. 7 and 8, or it can be in the form of a thin layer of film such as might be located on the surface 11' in FIG. 2; and in any of the gas, liquid or solid mediums, the shock wave can even detonate an explosion. It is to be appreciated that the disruptive or dividing forces discussed in this paragraph have some or probably greatest use in connection with chemical acts, such as the cracking process before mentioned, rather than the strictly biological aspects, but the biological aspects are of some importance.

In FIG. 16 incident radiation 23 from the laser 9 is delivered or directed upon the target 3 and the scattered or transmitted radiation from the target, labeled 50 in the figure is picked up by a detector 51. In this way, the nature of the macromolecular species in the target area and the effect thereon of the laser radiation is determined by measuring the scattered or transmitted or reflected radiation 50 as a function of frequency amplitude, and time. The detector 51 can be connected to a feedback control 52' to modify appropriately the output of the laser 9. The detector 51 can be gold-doped germanium or copper-doped germanium or a pyroelectric detector. Also, the detector 51 could activate an alarm 51' or other like device in the event of failure of the laser or other vital elements of the system, and this type arrangement can be included in the circuitry of FIGS. 5,6,7 and 8. Also, the biological or chemical activity of different macromolecular species can be altered selectively by varying the frequency and/or amplitude of the laser beam, and this too can be monitored.

A number of terms are used herein to denote similar actions, but the terms are not necessarily identical. The term "alter" is used to define a situation wherein molecules are activated or a situation wherein molecules are deactivated. The term "deactivate" is used to embrace "denaturation" as well as "inactivation" although the former is more properly concerned with protein cells and the latter is more properly concerned with bacteria generally. The term "activate" is intended to embrace, among other things, a catalytic effect which may, by way of illustration, accelerate or make possible a chemical reaction such as the cracking of petroleum before discussed.

Further modifications of the invention will occur to persons skilled in the art.

What is claimed is:

1. A method of altering the biological and/or chemical activity of macromolecular species by irradiation, that comprises, generating laser radiation at a frequency which delivers energy to said species by either directly or indirectly exciting vibrational and/or rotational states of the irradiated species, and directing said radiation upon the macromolecular species, said frequency being in the infrared frequency range.

2. A method as claimed in claim 1 that includes the further steps of disposing the species upon a reflective surface, directing the radiation at an oblique incident angle to the surface, and controlling the frequency of radiation to lie between three and thirty microns.

3. The method of claim 2 that includes the further step of detecting at least one of scattered, transmitted and reflected radiation, the nature of the macromolecular species and the effect thereon of the laser radiation being determined by measuring at least one of scattered, transmitted and reflected radiation as a function of at least one of frequency, amplitude and time.

4. A method as claimed in claim 1 in which the species is disposed upon a material which absorbs radiation at said frequency and in which the time of exposure to the radiation is long enough to effect said species both directly and indirectly through interaction of the species with said material but not long enough to cause undesirable damage to said material.

5. A method as claimed in claim 1 in which the species is disposed on an absorbent material and in which the level of intensity of said radiation or time of exposure, or a combination thereof, is adjusted to a level which will alter the biological and/or chemical activity of said species both directly or indirectly through interaction of the species with said material but below magnitudes sufficient to cause undesirable damage to the absorbing material.

6. A method of altering the biological or the chemical activity of molecular species by irradiation, that comprises, generating laser radiation at a frequency which selectively excites vibrational and rotational states of the irradiated species, directing said laser radiation upon the molecular species, said laser radiation being adjusted to lie in a range from about 350 $cm^{-1}$ to about 3,500 $cm^{-1}$, and controlling the frequency and at least one of the intensity and the time duration of the laser radiation to cause said altering of the biological or the chemical activity selectively to occur and to selectively control the level of said activity.

7. A method as claimed in claim 6 in which said chemical activity is a cracking process wherein complex molecules are broken down into less complex molecular structures and in which the radiation is used to activate a catalytic effect.

8. A method as claimed in claim 6 in which the frequency and at least one of the intensity and the time duration of the irradiation are controlled to cause said irradiation to influence catalytic action in a chemical reaction whereby the reaction can be made to occur with greater facility.

9. A method as claimed in claim 6 that includes exposing the molecular species to a catalyst and effecting catalytic action and in which at least one of the intensity and time duration of the irradiation is controlled to cause said irradiation to influence catalytic action and thereby affect said altering.

10. A method as claimed in claim 6 in which said frequency is tuned to an appropriate value to effect non-linear coupling of the radiation to a vibrating molecular band of the species.

11. A method of altering the structure of molecules, that comprises, subjecting the molecules to laser radiation at a frequency that is characteristic of the binding force between the constituents of the molecules, thereby to introduce a disruptive effect to said binding force, controlling said frequency and at least one of the intensity and the time duration of the laser radiation of influence in a determined fashion the level of said disruptive effect, and simultaneously applying a dividing force between the constituents to separate one from the other during the occurrence of said disruptive effect, said frequency being in the range from about 350 $cm^{-1}$ to about 3,500 $cm^{-1}$.

12. A method as claimed in claim 11 that includes subjecting the molecules to a high magnetic background field having a very high magnetic field gradient to provide said dividing force.

13. A method as claimed in claim 11 that includes subjecting the molecules to a high electric background field having a very high electric field gradient to provide said dividing force.

14. A method as claimed in claim 11 that includes subjecting the molecules to a high stress in the form of a shockwave to provide and enhance said dividing force.

15. A method of selectively removing one or more molecular layers of tissue and the macromolecular contaminants thereon, that comprises, generating laser radiation and controlling the amplitude, frequency and time duration of such radiation, and exposing the tissue to the laser radiation, the amplitude, frequency and time duration of which radiation is adapted to deliver energy to the vibrational and/or rotational states of the irradiated tissue and contaminants in sufficient amount to alter the biological activity thereof, said frequency being in the range from about 350 $cm^{-1}$ to about 3,500 $cm^{-1}$.

16. A method as claimed in claim 15 in which the radiation is generated by a $CO_2$ laser, the time duration is maintained at less than $10^{-1}$ seconds, and the power level is adjusted to be greater than 10 watts.

17. A method of altering by irradiation the biological and/or chemical activity of macromolecular species which are a constituent of a liquid, that comprises, generating laser radiation at a frequency which delivers energy to said species by exciting vibrational and/or rotational states of said species either directly or indirectly, and directing said radiation upon the macromolecular species, said frequency being in the infrared frequency range.

18. A method as claimed in claim 17 that includes providing reflecting bodies dispersed in the liquid to effect a spreading of incident radiation therein.

19. A method as claimed in claim 17 in which the alteration of biological and/or chemical activity is a pasteurization of the liquid.

20. A method as claimed in claim 17 in which the liquid is at least partially transparent to the irradiating beam.

21. A method of destroying living cells, spores and other like macromolecular species to effect sterilization, that comprises applying to the species laser radiation that is characteristic of the bonding force between various constituents of the species thereby to provide a disruptive effect to said bonding force and to allow other disruptive forces to affect such species to cause the species to change their spatial configuration and thereby be destroyed, said laser radiation being adjusted to lie in a range from about 350 $cm^{-1}$ to about 3,500 $cm^{-1}$.

22. A method as claimed in claim 21 that includes controlling the frequency, amplitude and time exposure of the radiation, thereby selectively to deactivate one or more macromolecular species of a group of said species.

23. A method as claimed in claim 21 in which the radiation is generated by a $CO_2$ laser, the time duration is maintained at less than $10^{-1}$ seconds, and the power level is adjusted to be greater than 10 watts.

24. A method as claimed in claim 21 in which the time duration is adjusted to the nanosecond range and the power level of the generated laser radiation is provided in the megawatt range.

25. A method of destroying living cells, spores, and other like macromolecular species to effect sterilization of a medium contaminated with said species, which comprises applying to the species laser radiation that is characteristic of the bonding force between various constituents of the species thereby to provide a disruptive effect to said bonding force and to allow other disruptive forces that affect such species to cause the species to change their spatial configuration and thereby be destroyed, the laser radiation being applied at a frequency which lies in a range from about 350 $cm^{-1}$ to about 3,500 $cm^{-1}$.

26. A method as claimed in claim 25, wherein the laser radiation is varied in amplitude and/or frequency, thereby selectively to affect particular macromolecular species while having a lesser effect upon others, and which includes the further step of detecting at least one of scattered, reflected, and transmitted radiation from the species to determine the effect thereupon of the radiation.

27. A method as claimed in claim 25, which includes the further steps of disposing the species upon a reflective surface, directing the radiation at an oblique incident angle to the surface, and controlling the frequency of radiation to lie between 3 and 30 microns.

28. A method of destroying by irradiation living cells, spores, and other like macromolecular species to effect sterilization of a medium contaminated with said species, which comprises generating laser radiation at a frequency which excites vibrational and rotational states of the irradiated species either directly or indirectly, and directing said laser radiation upon said species thereby to effect sterilization of the medium, said laser radiation being adjusted to lie in a range of from about 350 $cm^{-1}$ to about 3,500 $cm^{-1}$.

29. A method as claimed in claim 28 in which the medium is flesh.

30. A method as claimed in claim 28 in which the medium is the surface tissue selected from the group consisting of vegetables, fruit, fish, meat and other foodstuffs.

31. A method as claimed in claim 28 in which the medium is selected from the group consisting of cloth, paper, glass, and plastics.

32. A method of altering by irradiation the biological and/or chemical activity of compounds selected from the group consisting of nucleic and amino acids, which comprises generating laser radiation at a frequency which excites vibrational and/or rotational states of the irradiated species, and directing said laser radiation upon said species, said frequency being in the infrared frequency range.

33. A method as set forth on claim 32, in which frequency is adjusted to lie in a range from about 350 $cm^{-1}$ to about 3,500 $cm^{-1}$.

34. A method as claimed in claim 33 in which the radiation is generated by a $CO_2$ laser, the time duration is maintained at less than $10^{-1}$ seconds, and the power level is adjusted to be greater than ten watts.

35. A method as claimed in claim 33 in which the time duration is adjusted to the nanosecond range and the power level of the generated laser radiation is provided in the megawatt range.

36. A method of altering the biological or the chemical activity of molecular species by irradiation, that comprises, generating laser radiation at a frequency which selectively excites vibrational states of the irradiated species, directing said laser radiation upon the molecular species, adjusting said laser radiation to lie in the infrared frequency range, tuning said frequency to an appropriate value to effect non-linear coupling of the radiation to a vibrating molecular bond of the species, and controlling at least one of the intensity and the time duration of the laser radiation to cause said altering of the biological or the chemical activity to occur and to control the level of said activity.

* * * * *